United States Patent [19]
Soni et al.

[11] Patent Number: 5,363,850
[45] Date of Patent: Nov. 15, 1994

[54] METHOD FOR RECOGNITION AND REDUCTION OF BLOOD SPECKLE IN BLOOD VESSEL IMAGING SYSTEM

[75] Inventors: Bobby Soni, Campbell; Richard Didday, Soquel; Kean Hurley, Watsonville, all of Calif.

[73] Assignee: Cardiovascular Imaging Systems, Inc., Sunnyvale, Calif.

[21] Appl. No.: 187,584

[22] Filed: Jan. 26, 1994

[51] Int. Cl.$^5$ .............................................. A61B 8/00
[52] U.S. Cl. ......................... 128/661.08; 128/660.05; 128/662.02; 128/662.06; 128/916
[58] Field of Search ............... 128/660.05, 661.08, 128/661.09, 661.10, 662.01, 662.02, 662.06, 916

[56] References Cited
U.S. PATENT DOCUMENTS

| | | |
|---|---|---|
| 4,794,931 | 1/1989 | Yock . |
| 5,000,185 | 3/1991 | Yock . |
| 5,224,483 | 7/1993 | Lipschutz .................. 128/662.02 |
| 5,243,988 | 9/1993 | Sieben et al. ............... 128/661.08 |
| 5,285,788 | 2/1994 | Arenson et al. ............. 128/660.05 |

*Primary Examiner*—George Manuel
*Attorney, Agent, or Firm*—Townsend and Townsend Khourie and Crew

[57] ABSTRACT

In an ultrasound imaging system, ultrasound echoes representing vessel walls are distinguished from ultrasound echoes from blood by using a classifier which employs the mean and variance of the raw data of gray intensities as acquired directly from an ultrasound scanner detector. In a specific embodiment, the statistical parameters of mean and variance are determined in the course of real-time processing and prior to attempted classification and then are used as parameters representing the true image as acquired.

6 Claims, 4 Drawing Sheets

METHOD FOR RECOGNITION AND REDUCTION OF BLOOD SPECKLE IN BLOOD VESSEL IMAGING SYSTEM

BACKGROUND OF THE INVENTION

This invention relates to high resolution intravascular imaging and more particularly to ultrasound imaging and techniques for enhancing image quality.

In ultrasound imaging, echoes from blood molecules degrade the lumen-to-vessel wall contrast. However, the production of high resolution images of vessel wall structures requires imaging at high ultrasound frequencies. The back scatter from blood in such an image is a significant problem in high frequency ultrasound imaging, since the scattering of ultrasound from blood is proportional to the fourth power of the frequency such that the higher the ultrasound frequency the more pronounced is the back scatter from blood.

It is desirable to provide imaging over a broad range of frequencies. Therefore, echoes in the ultrasound image due to blood cells must either be removed or suppressed to a level at which wall structures can be distinguished from blood. Since blood is typically in motion relative to the image of interest, an individual frame will contain speckle due to the interference of blood constituents. One technique for enhancing image quality is to average successive image frames thereby to smooth out the impact of speckle (that is, the irregular pattern of backscatter from blood cells) in the ultrasound images. Thresholding-based techniques have been suggested wherein blood-speckle induced smearing is removed based on a signal intensity compared with a threshold. However, such techniques are not effective in reducing the mean echo amplitude from the region of blood flow, and they cannot totally remove blood echoes from the image. What is needed is a mechanism for identifying the signatures of blood-induced echoes and for subsequently suppression which allows a display of ultrasound images free of blood-induced echoes.

Background information on the subject of intravascular ultrasonography is found in U.S. Pat. No. 4,794,931 and related U.S. Pat. No. 5,000,185.

SUMMARY OF THE INVENTION

According to the invention, in an ultrasound imaging system, ultrasound echoes representing blood vessel walls are distinguished from ultrasound echoes from blood. This is achieved by using a classifier which employs the mean and variance of raw data of gray intensities as acquired directly from an ultrasound scanner detector. In a specific embodiment, the statistical parameters of mean and variance are determined in the course of real-time processing and prior to attempted classification and then are used as parameters representing the true image as acquired.

Parameters are computed by first obtaining an image, then distinguishing between the blood region as opposed to the wall region by statistical analysis, namely, obtaining a mean and variance at candidate positions, multiplying the mean by the variance to obtain a "factor" and noting that the product of mean and variance of a blood region is substantially higher than the product of the mean and variance of a wall region. As a result, a user can control the appearance of the blood region of the image.

The invention will be better understood by reference to the following detailed description in connection with the accompanying drawings.

DESCRIPTION OF SPECIFIC EMBODIMENTS

Figure 1:
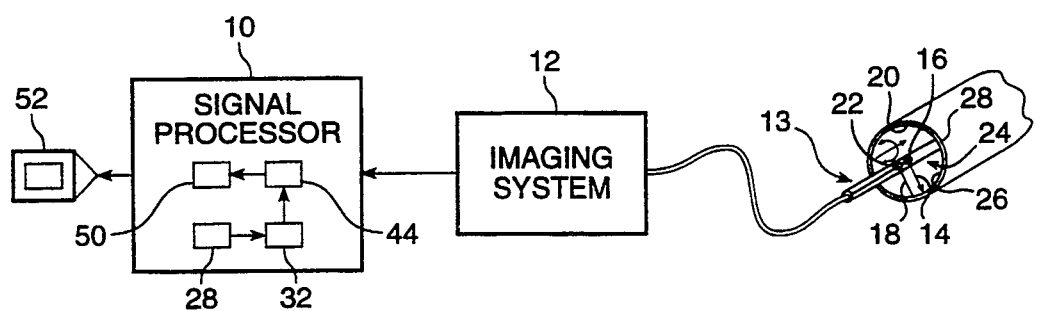
FIG. 1 is a block diagram of an intravascular ultrasonic imaging system in accordance with the invention.

The invention may be understood by reference to the FIGS. 1 through 5. A specialized signal processing device 10 is used with an ultrasonic imaging system 12 including a catheter probe 13 wherein ultrasonic beams 14 are emitted by an exciter 16, and spokes or vectors 18 of information are collected from a target 20 (the interior walls of a blood vessel) based on ultrasonic reflections at a transducer 22. The reflections scale in amplitude over a range, and pixels representing points in a scanned (swept and pulled out) two-dimensional image are assigned a value on a gray scale between opaque to transparent. The image is representative of a "slice" of the structure of blood vessel 20 and includes wall structures and lumens of blood.

More specifically, information is gathered by projecting narrow ultrasonic sampling beams 14 from exciter 16 as it is rotated within catheter 13 within blood vessel 20, the reflections of which are recorded by transducer 22 as amplitude as a function of distance along the radius of each vector. "Factors" are computed at every unit radius in a sampling window (e.g., five by five pixels in size). Depending upon the absolute value of the factors along the entire radius of each reflected spoke (vector) 18, the end of the spoke 18 is identified as lying entirely within the blood region 24 or at the blood-wall interface 26 or within the vessel wall 28 or at some indeterminant position 30 beyond the vessel wall 28. So long as a reasonable length of a sampling spoke is determined to be within a known region, such as the blood region, the information gathered from the sampling spoke 18 is used to determine a mean value and a variance value useful for calculation purposes as hereinafter explained. A total of eight spokes radially directed from the catheter 13 is generally sufficient to obtain data to process the information. Using the accumulated information from as many as all eight spokes, the average mean and average standard deviation (variance) are determined.

Figure 4:
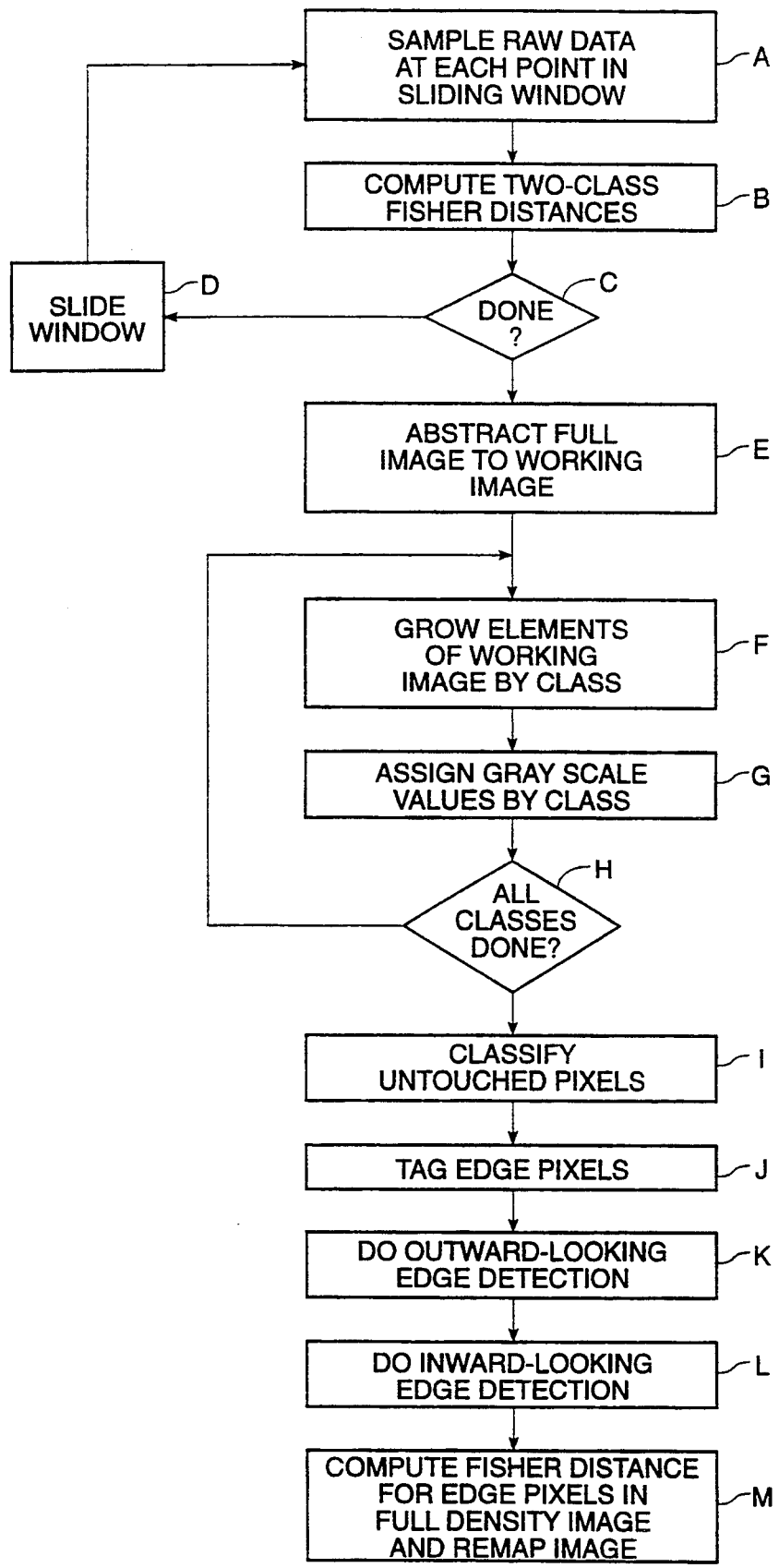
FIG. 4 is a flow chart of the method according to the invention.

Referring to FIG. 4, as a first estimation of the (location of the) blood region and the wall region in a volume image, the raw image data is sampled for every point using a local neighborhood, where the size of the window is relatively dense, e.g., eleven by eleven pixels (Step A). Then for each point a distance metric is evaluated for a two-class problem, the two classes being blood region and wall region (Step B). In a specific embodiment, the distance metrics are "Fisher" distances. Other distance metrics may be employed, such as a least squares distance metric. The "Fisher" distance metric is preferred because it takes into account statistical variance. The "Fisher" distances are represented by the following equations:

$$d_1 = (x_{ij} - m_1)^2 / \text{var}_1 \quad \text{(Eq. 1)}$$

$$d_2 = (x_{ij} - m_2)^2 / \text{var}_2 \quad \text{(Eq. 2)}$$

where:
$X_{ij}$ is the gray scale intensity of the (i,j)th pixel;
$m_1$ is the mean of class 1;
$\text{var}_1$ is the variance of class 1;
$m_2$ is the mean of class 2; and
$\text{var}_2$ is the variance of class 2.

The decision rule for determining whether a pixel with Fisher distance $d_x$ belongs to class 1 or to class 2 is given by:
If ($d_1$ is less than $d_2$), then the (i,j)th belongs to class 1; otherwise the (i,j)th pixel belongs to class 2.

These Fisher distances are computed for every point within the sampling window. Votes are accumulated for the window for both the blood region class and the wall region class, depending whether the pixel is classified as belonging to "blood" or "wall". If the percentage of pixels classified as blood within the sampling window is more than the empirically-estimated threshold, then the center pixel of the window is classified as belonging to the blood region. Otherwise the center pixel is classified as belonging to the wall region. Thereafter the window is moved (by one pixel) (Steps C, D), and the center pixel is again classified (repeating Steps A and B). The entire image is thus processed with overlapping windows, segmenting each window into the two classes.

A local binary copy of the image is maintained in memory of the signal processing device 10 with each pixel belonging to either to the wall region or the blood region. A pullback (longitudinal displacement of the tranducer along the blood vessel) is performed to produce a series of sliced images. Then the Fisher distances are computed for each slice, and the pixels of each image slice are classified so that a set of binary images is obtained.

Figure 2:
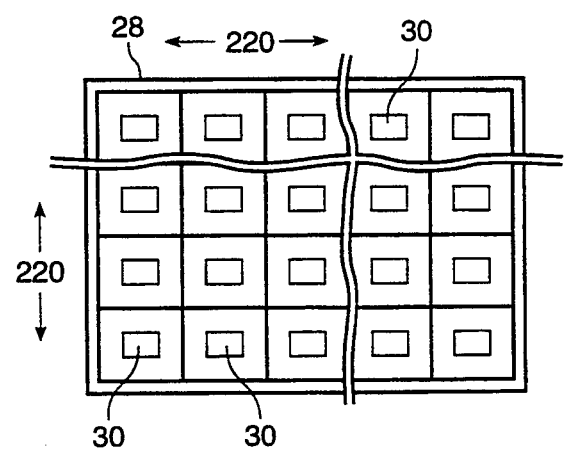
FIG. 2 is a representative diagram of an array of a full density pixel image.
Figure 3:
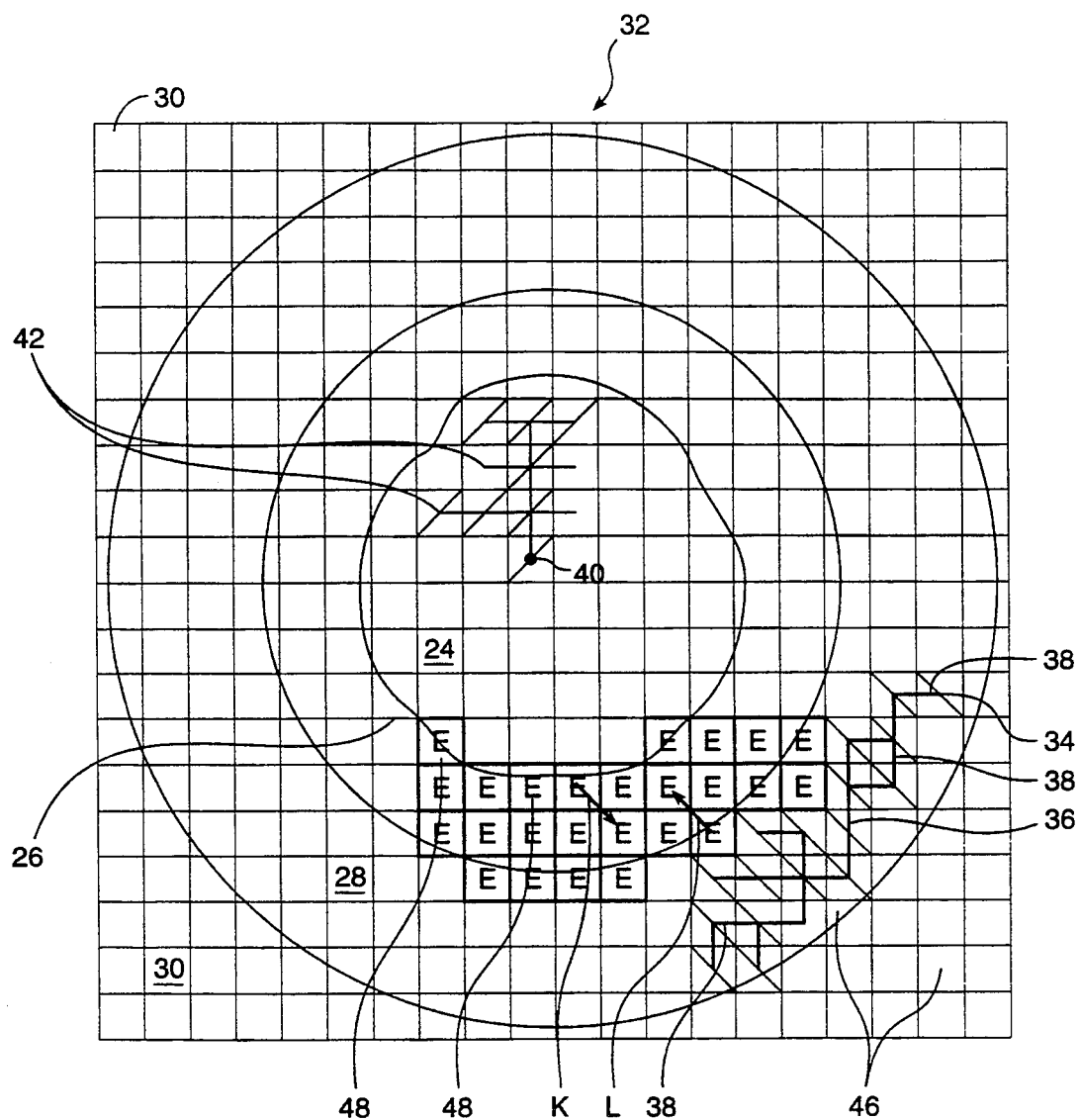
FIG. 3 is a representative diagram of an array of a working image.

After the first estimation is made, knowledge of blood vessel morphology is used to refine the initial binary classification of each pixel in each sliced image. (Up to 150 slices are processed, preferably within sixty seconds time, to obtain information which is sufficiently time invariant to be clinically significant.) The initially processed binary image (of one slice) 28 comprises an array of pixels measuring 220 by 220 pixels (FIG. 2—not all pixels shown). According to the invention, the initial binary image 28 (FIG. 2), which is typically too cumbersome to be subjected to a long and complex calculation) is sampled or abstracted at a low density of for example, one pixel per eleven pixels of the initial image 28 to yield an abstracted image or working image 32 (FIG. 3) of for example twenty by twenty pixels, each pixel in the abstracted image 32 representing an eleven by eleven group of the full image 28 (Step E). This working image 32 is also stored in the image processing device 10 for manipulation.

Then, based on knowledge of morphology, e.g., assuming that the lumen under examination is enclosed by the wall tissue 28 in the probed vessel structure or target 20, the working image 32 is modified, namely, a region therein is reconstructively "grown" from a seed point 34, if a growth path 36 exists of connected pixels 38 of the same class (Step F). As a seed point 40 for the lumen, a pixel in the center of the transducer 22 (FIG. 1) may be selected, thus assuring that the seed point is in the blood region 24 in the image 32. Pixels considered to be in the blood region are tagged as being "interior" pixels 42. These pixels are then assigned a distinct gray scale value in a reconstruction 44 of abstracted image 32 stored also in the signal processing device 10 (Step G).

The inventive process is employed to develop a viewable image of the other types of morphological elements (Step H, F, G). Wall seed point 34 is selected so as to "grow" to include all connected pixels 38 of the abstracted image which belong to the "wall" class. The growing procedure yields the connections, and the wall pixels 38 in the abstracted or working image 32 are so tagged as being "exterior" and assigned a distinct gray scale value different from the lumen-assigned gray scale value in the reconstruction 44 (FIG. 1).

An intermediately-processed abstracted image (intermediate reconstruction 44) then consists of interconnected interior pixels 42, interconnected exterior pixels 38 and untouched unclassified pixels 46. The untouched pixels thereafter need to be classified. They are classified by checking the classification of their neighbors and then assigning to them the classification of their immediate neighbors (Step I).

As a next step, edge pixels 48 comprising the interface between the lumen and the wall must be processed. The resolution of the abstracted image is generally insufficient to classify such points correctly. The edge pixels must therefore be at least initially tagged as being edge pixels, that is, as being neither interior nor exterior An edge detection processing technique is applied to the image to look for transitions from interior points to exterior points. Pixels found between interior points and exterior points are first tagged as edge pixels (Step J). The edge detection processing technique is first applied from the blood region looking out (Step K). Then the edge detection processing technique is applied from the wall region looking in (Step L).

The classified abstracted image or reconstruction 44 is thereafter remapped into a full resolution gray scale image 50 (Step M), with the following rules applied to assignment of gray scale values:

1) If the pixel in the reconstructed image is tagged as being an exterior point, then the corresponding (surrounding) pixels of the full resolution image are assigned the original gray scale value of the raw image.
2) If the pixel in the reconstructed image is tagged as being interior, then the corresponding (surrounding) pixels of the full resolution image are presumed to be blood and the gray scale value is set to zero or some other high contrast value which is a percentage of the original gray scale intensity.
3) If the pixel in the reconstructed image is tagged as an edge pixel, then the Fisher classification for the high resolution pixels in the full resolution image is used to identify the pixels as either in the blood region or the wall region, and the corresponding gray scale value is assigned to the resultant high resolution pixel.

In this manner, a high resolution image is obtained for display on a display device 52 with sharp edge identification, while minimizing the amount of required computation of Fisher distances.

Figure 5:
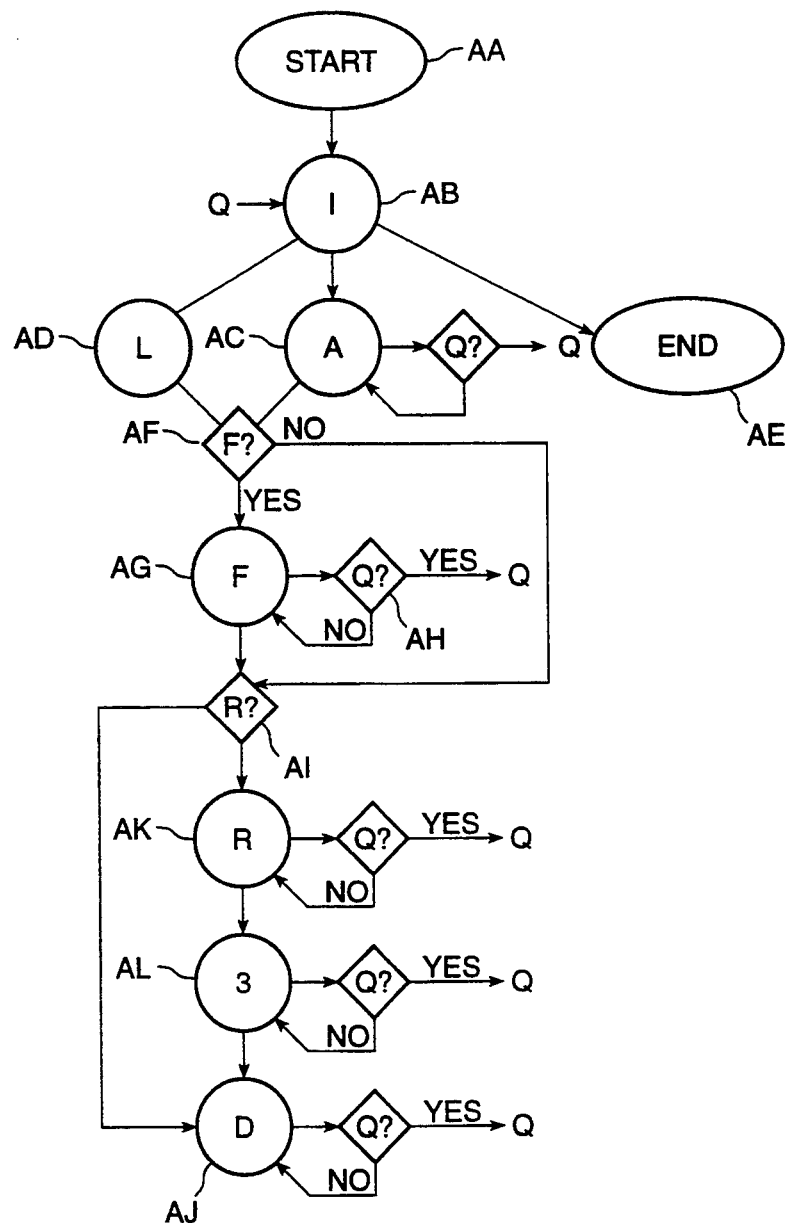
FIG. 5 is a flow chart of a general method of processing in accordance with the invention.

FIG. 5 is a flow chart of program flow according to the invention. After start or following a "quit" state (Step AA), the system is initialized (Step AB), and it acquires data (Step AC), or alternatively is calibrated (Step AD) or is terminated (Step AE). After testing for the need for the Fisher Algorithm (Step AF), it either iteratively applies the algorithm (Steps AG, AH) and quits, or applies it and tests for the requirement of a rendering process (Step AI). The system either skips to the display step (Step AJ) or performs a rendering and a 3D animation (Steps AK, AL), after which it displays the results (Step AJ).

There are several possible switches or options to the processing: To step through raw data or to display a three-dimensional movie; to save raw data or to display the three-dimensional movie; or to animate the raw data or display a three-movie.

While the invention has been particularly shown and described with reference to preferred embodiments thereof, it will be understood by those skilled in the art that the foregoing and other changes in the form and details may be made therein without departing from the spirit or scope of the invention. For example, variants on the distance metric may be employed. It is therefore not intended that this invention be limited, except as indicated by the appended claims.

What is claimed is:

1. A method for enhancing an intravascular ultrasonic blood vessel image comprising the steps of:
   a) illuminating an intravascular target from within a blood vessel with ultrasonic energy to generate ultrasonic echoes from said intravascular target; thereafter
   b) intercepting the ultrasonic echoes from the intravascular target;
   c) transforming the ultrasonic echoes into electrical signals;
   d) forming and constructing an image based on amplitude of each said electrical signals, by illuminating and sweeping said intravascular target and by circumferentially and radially sampling the electrical signals, assigning an initial gray scale value to each increment (pixel) in said image;
   e) computing a distance metric for each pixel using seed values for each said pixel;
   f) sampling said image to obtain a sampled image;
   g) growing a first interior classification for points in said a sampled image from a first seed pixel preselected to be entirely within a first region of a first known class;
   h) growing a second exterior classification for exterior points from a second seed pixel in a second region of a second known class;
   i) identifying and classifying other pixels in the a sampled image by searching for points between interior classified pixels and exterior classified pixels and tagging said other pixels as said edge pixels;
   j) remapping all interior pixels, exterior pixels and edge pixels so classified into a full resolution image
      1) by mapping exterior pixels with first gray scale values, 2) by mapping interior pixels with second gray scale values and 3) by mapping edge pixels according to a high resolution Fisher classification for said edge pixels; and
   k) outputting said full resolution image for display.

2. The method according to claim 1 wherein said step a) comprises illuminating the intravascular target with a plurality of beams radially-directed as spokes around a central point, and incrementally advancing the central point along an intravascular axis so as to generate information to construct a three-dimensional image.

3. The method according to claim 2 wherein said sampling step comprises collapsing said three-dimensional image by a factor which yields said sampling image with minimum detail sufficient to identify and classify between a blood region and a vessel wall region.

4. The method according to claim 1 wherein said sampling step comprises collapsing said full resolution image by a factor which yields said a sampled image with minimum detail sufficient to identify and classify between a blood region and a vessel wall region.

5. The method according to claim 4 wherein said distance metric computing step comprises computing a Fisher distance for each pixel using said seed values of mean and variance to obtain a Fisher classification.

6. The method according to claim 1 wherein said distance metric computing step comprises computing a Fisher distance for each pixel using said seed values of mean and variance to obtain a Fisher classification.

* * * * *